United States Patent [19]

Rossignol

[11] Patent Number: 5,856,348

[45] Date of Patent: *Jan. 5, 1999

[54] METHOD FOR TREATMENT OF TREMATODES WITH PHARMACEUTICAL COMPOSITIONS OF TIZOXANIDE AND NITAZOXANIDE

[75] Inventor: Jean-Francois Rossignol, Clearwater, Fla.

[73] Assignee: Romark Laboratories, L.C., Tampa, Fla.

[ * ] Notice: The term of this patent shall not extend beyond the expiration date of Pat. No. 5,578,621.

[21] Appl. No.: 887,810

[22] Filed: Jul. 3, 1997

Related U.S. Application Data

[63] Continuation-in-part of Ser. No. 644,153, May 10, 1996, Pat. No. 5,859,038, Ser. No. 852,447, May 7, 1997, and Ser. No. 847,130, May 1, 1997, abandoned, which is a continuation of Ser. No. 383,855, Feb. 6, 1995, abandoned, said Ser. No. 644,153, is a continuation-in-part of Ser. No. 301,407, Sep. 8, 1994, Pat. No. 5,578,621.

[51] Int. Cl.⁶ .................................................. A61R 31/425
[52] U.S. Cl. ............................................................ 514/371
[58] Field of Search ............................... 548/192; 514/371

[56] References Cited

FOREIGN PATENT DOCUMENTS

95/28393 10/1995 WIPO ..................................... 548/192

Primary Examiner—Robert Gerstl
Attorney, Agent, or Firm—Pendorf & Cutliff

[57] ABSTRACT

Methods for treatment of a parasitic infection of a trematode selected from the group consisting of Schistosoma such as *Schistosoma mansoni*, *Schistosoma haematobium*, *Schistosoma mekongi*, *Schistosoma japonicum*, and *Schistosoma intercalatum*, Fasciola such as *Fasciola hepatica* and *Fasciola gigantica*, *Fasciolopsis buski*, *Dicrocoelium dendriticun*, *Heterophyes heterophyes*, and *Metagonimus yokogawa*, the methods comprising administration of a pharmaceutical composition containing as active agent at least one compound selected the group consisting of a compound of formula I:

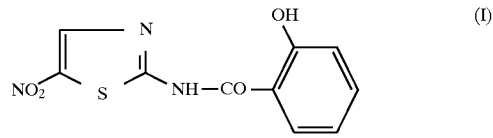

and a compound of formula II:

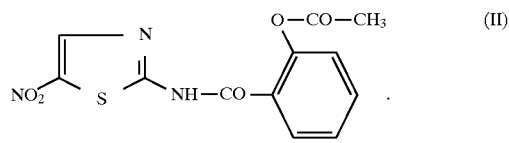

25 Claims, No Drawings

METHOD FOR TREATMENT OF TREMATODES WITH PHARMACEUTICAL COMPOSITIONS OF TIZOXANIDE AND NITAZOXANIDE

CONTINUATION DATA

This application is a continuation-in-part, of U.S. application Ser. No. 08/644,153 filed May 10, 1996, now U.S. Pat. No. 5,859,038, which is a continuation-in-part of U.S. application Ser. No. 08/301,407 filed Sep. 8, 1994, now U.S. Pat. No. 5,578,621; and a continuation-in-part of U.S. application Ser. No. 08/847,130 filed May 1, 1997, now abandoned, which is a continuation of U.S. application Ser. No. 08/383,855 filed Feb. 6, 1995, now abandoned; and a continuation-in-part of U.S. application Ser. No. 08/852,447 filed May 7, 1997.

BACKGROUND OF THE INVENTION

1. Field of the Invention

The present invention relates to a methods for treatment of infections of Schistosoma such as *Schistosoma mansoni, Schistosoma haematobium, Schistosoma mekongi, Schistosoma japonicum*, and *Schistosoma intercalatum*, Fasciola such as *Fasciola hepatica* and *Fasciola gigantica, Fasciolopsis buski, Dicrocoelium dendriticum, Heterophyes heterophyes*, and *Metagonimus yokogawa*, the method comprising administration of a pharmaceutical composition containing as active agent a compound selected from the group consisting of a desacetyl-nitazoxanide and nitazoxanide.

2. Description of the Related Art

Many parasitic infections prevalent in humans are difficult to treat. *Schistosoma mansoni*, the blood fluke, is the causative agent of Schistosomiasis (Bilharziosis, Bilharziose), the second most important tropical parasitic disease of man (after Malaria), and the most important trematode infection of man. *Schistosoma haematobium* is another important species infecting man. Over 200 million individuals suffer from schistosomiasis world wide, including several hundred thousand people in the United States. The disease is spreading due to technological advances and irrigation programs in underdeveloped countries. Humans are actively invaded by the waterliving cercariae of the parasite, which are emitted from water snails. The snails are actively invaded by miracidia, which originate from eggs, released from the human hosts into water. Pathology associated with infection is not caused by direct activity of the parasite, but rather by immunological and inflammatory responses of the host. There is no treatment for dermatitis or Katayame syndrome associated with infection, but praziquantel is reportedly effective against schistosomes.

*Fasciola hepatica*, the common liver fluke, is primarily a disease of sheep. However, humans are an accidental host acquiring infectious metacercariae through consumption of contaminated water, aquatic grasses or watercress. In the United States *Fasciola hepatica* is enzootic in extensive areas in the southern, southeastern, southwest, west and north central United States. The adult worms live in the bile ducts and release their eggs into the lumen of the intestine, which are then evacuated with feces. When eggs get into water the ciliated miracidia hatch and find a suitable intermediate host snail. After successful penetration of the intermediate host they develop through sporocyst and redial stages to cercariae which are shed from the snail. The free-swimming larvae attach themselves to firm surfaces like grass blades and form encysted metacercariae which are infective for several months under favorable circumstances.

When shallow fresh water vegetation is ingested by the final host, the metacercariae excyst in the small intestine, migrate through the gut wall, cross the peritoneum and penetrate the liver capsule. After tunneling through the parenchyma for several weeks the young flukes migrate to the bile ducts and occasionally to the gall bladder and become mature. The parasite manages to survive in the presence of a vigorous host immune response. Symptoms associated with migration include epigastric pain, abdominal tenderness, urticaria and high-level eosinophilia. Bithionol has been suggested for treatment, but is not approved for use in the United States.

SUMMARY OF THE INVENTION

The present invention is based on the surprising discovery of the consistent and optimal efficacy of method for treatment of infection of Schistosoma such as *Schistosoma mansoni, Schistosoma haematobium, Schistosoma mekongi, Schistosoma japonicum*, and *Schistosoma intercalatum*, Fasciola such as *Fasciola hepatica* and *Fasciola gigantica, Fasciolopsis buski, Dicrocoelium dendriticum, Heterophyes heterophyes*, and *Metagonimus yokogawa*, in animals and humans, the method comprising administration of a pharmaceutical composition containing as active agent a compound selected the group consisting of a desacetyl-nitazoxanide and nitazoxanide.

The pharmaceutical composition may be in a form suitable for oral administration, as a solid dosage form, a liquid suspension, or a paste.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other pharmaceutical compositions and methods for treatment for carrying out the same purposes of the present invention. It should also be realized by those skilled in the art that such equivalent formulations and methods do not depart from the spirit and scope of the invention as set forth in the appended claims.

DETAILED DESCRIPTION OF THE INVENTION

The method for treatment of Schistosoma such as *Schistosoma mansoni, Schistosoma haematobium, Schistosoma mekongi, Schistosoma japonicum*, and *Schistosoma intercalatum*, Fasciola such as *Fasciola hepatica* and *Fasciola gigantica, Fasciolopsis buski, Dicrocoelium dendriticum, Heterophyes heterophyes*, and *Metagonimus yokogawa* infections of the present invention comprises administration of a pharmaceutical composition comprising, as active agent, a compound selected from the group consisting of desacetyl-nitazoxanide of formula I:

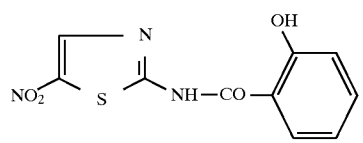

and nitazoxanide of formula II:

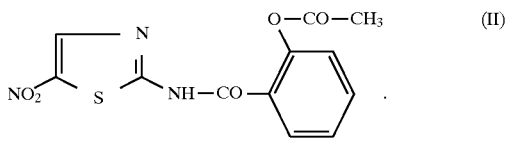

Nitazoxanide, the compound of formula II, sometimes referred to hereafter as NTZ or compound PH 5776, is the generic name for 2-(acetolyloxy)-N-(5-nitro 2-thiazoly) benzamide, a compound first synthesized by Rossignol and Cavier in 1975 and subsequently shown to have activity against a number of protozoan and helminthic pathogens. Nitazoxanide has a molecular weight of 307.2; it appears as odorless yellow granules with a melting pint of 202°–204° C.; it is very poorly soluble in water, either and methyl benzene; poorly soluble in ethanol, chloroform and acetic acid; fairly soluble in dioxane and acetone and easily soluble in pyridine. Solubilisation in DMSO is recommended.

In 1980, Euzeby et al reported the cestocidal effect of a single oral dose of nitazoxanide against *Moniezia expansa, Avitellina centripunctata, Stilesia globipunctata* and *Taenia taeniaeformis* in cats. In addition, when using repeated doses of the drug, efficacy against gastrointestinal nematodes of dogs such as *Uncinaria stenocephala* and *Trichuris vulpis* was also observed. In 1982 Cavier and Rossignol reported the single dose activity of nitazoxanide against *Hymenolepis nana* in mice and the effect of repeated doses of the drug against *Syphacia obvelata* in mice. More recently Dubreuil et al. reported that nitazoxanide was also effective against Gram positive bacteria such as *Staphylococcus aureau* and facultative and obligate anaerobic Gram positive and Gram negate bacteria.

The preparation and certain uses of this compound are disclosed in U.S. Pat. No. 3,950,351, as well as in publications made by the present inventor.

Desacetyl-nitazoxanide, the compound of formula II, is sometimes referred to as tizoxanide or d-NTZ, and is a metabolite of nitazoxanide.

In WO 95/28393, the present inventor disclosed a method for the manufacture of pure compound of formula I, as well as the use of the composition containing a mixture of compounds of formula I and II.

The compound(s) of formula I and II may be administered in either a solid dosage form or an aqueous suspension, and it is preferred that the pharmaceutical composition contain the effective dose of the active agent in the form of solid particles having a particle size smaller than 200 μm and containing compound of formula I and/or compound of formula II, the mean particle size of the said active solid particles being greater than 10 μm as determined by a Coulter® Counter LS 100. This equipment uses laser light at 750 nm to size particles from 0.4 to 900 μm in diameter by light diffraction. The samples are measured in water with a small amount of Triton X-100 in order to increase the wettability and deflocculate the powder.

The solubility is 2 mg of nitazoxanide in 1 ml DMSO. Nitazoxanide is easily absorbed orally.

Advantageously, the mean particle size of the said active solid particles is between 10 and 100 μm, preferably between 20 and 50 μm. In accordance with a preferred embodiment of the composition, less than 10% of the said active solid particles has a particle size smaller than 5 μm.

The invention also relates to pharmaceutical compositions described above which contain advantageously at least one pharmaceutically acceptable acid. Examples of such acids are: citric acid, glutamic acid, succinic acid, ethanesulfonic acid, acetic acid, tartric acid, ascorbic acid, methanesulfonic acid, fumaric acid, adipic acid, malic acid and mixtures thereof. Citric acid is very appropriate. The presence of said acid improves the stability of the active agent or agents.

The ratio of the weight of pharmaceutically acceptable acid/the weight of said active solid particles is advantageously between 0.01 and 0.5, preferably between 0.03 and 0.2. Advantageously, the amount of acid is sufficient for adjusting a the pH of the suspension between 2 and 6, preferably between 3 and 5, most preferably between 3.5 and 4.5.

The active agent or agents used in the solid dosage form or suspension is advantageously a mixture of solid particles of compounds of formula I and of formula II with a particle size smaller than 200 μm, the weight content of compound of formula II with respect to the weight of compounds of Formula I and of Formula II of said mixture being comprised between 0.5 and 20%, preferably between 0.5 and 10%.

Techniques for preparation of, and preferred examples of, solid and liquid dosage forms of the pharmaceutical composition are disclosed in WO/95/28393, the disclosure of which is incorporated herein by reference. The compositions contain advantageously a wetting agent and possibly a starch derivative such as those disclosed in U.S. Pat. No. 5,578,621, the content of which is incorporated herein by reference for disclosing possible wetting agents and starch derivatives. The wetting agent as described in U.S. Pat. No. 5,578,621 serves as a dispersing agent.

Such pharmaceutical compositions, either as solid or liquid dosage forms or as pastes or ointments, can optionally contain additional active agents such as antibiotics, antiviral agents or proton pump inhibitors. While it is not advantageous, it is also possible that such pharmaceutical formulations may contain active solid particles of compound of Formula I and/or compound of Formula II which are larger than 200 μm.

The compositions can contain excipients known as such for the purpose of preparing forms suitable for oral administration. The efficacy and the safety of the pharmaceutical compositions disclosed hereabove were excellent in animals and in humans.

The pharmaceutical compositions described are suitable for treating human and animal infections caused by Schistosoma such as *Schistosoma mansoni, Schistosoma haematobium, Schistosoma mekongi, Schistosoma japonicum, Schistosoma intercalatum*, Fasciola such as *Fasciola hepatica* and *Fasciola gigantica, Fasciolopsis buski, Dicrocoelium dendriticum, Heterophyes heterophyes*, and *Metagonimus yokogawa*.

EXAMPLE I

The in vitro efficacy of nitazoxanide and desacetylnitazoxanide was tested against *Fasciola hepatica*.

Mature *F. hepatica* were recovered from the bile ducts of 3 calf livers condemned due to fasciolosis at the Louisiana Veterinary Medical Diagnostic Laboratory at the Hardy's Meat Packers, Bunkie, La. Flukes were washed in sterile saline for 1 hour and transferred to sterile saline or RPMI (pH 7.4) for an additional 3 hours. Flukes were then held in sterile RPMI-rabbit serum (50:50 v/v) or sterile RPMI (pH 7.4) overnight at 37° C. with 5% $CO_2$.

In vitro culture (37° C., 5% $CO_2$) was done according to a modification of the method of Ibarra and Jenkins (Z. Parasitenkd. 70:655–661, 1984). Using sterile technique, flukes were washed twice for 2–3 minutes in Hank's balanced salt solution (pH 7.2) and placed individually into wells of six-well Linbro culture plates containing 10 ml aliquots of the designated dilutions of the drug in culture media. The latter consisted of sterile 50:50 v/v RPMI-Rabbit serum with 2% Rabbit Blood plus 100 ppm Penicillin and 100 ppm Streptomycin. Only flukes that had normal activity and morphology were used.

Stock solutions of NTZ or its metabolite D-NTZ provided by Romark were dissolved in DMSO (2000 µg/ml) and diluted in culture medium, using 100 ml volumetric flasks, to produce the specified drug concentrations (100, 50, 25, 10, 5, 3, 1 µg/ml). Two control flukes were included in each replicate, one in unmediated culture media with RBC and one in unmedicated culture media with RBC.

Flukes were examined for the effects of drug treatment as evidenced by death, motility disturbances or morpholgic changes as compared to untreated control flukes, using a backlighted panel and a lighted 3× magnifying lens.

Results:

Experiment 1: For D-NTZ, flukes in the 50 and 100 µg treatments were moribund or dead within one hour. Four of 7 flukes in the 25 µg treatment were moribund, two were active, and one was sluggish within the first hour; all were dead except tow sluggish flukes by three hours and only one sluggish fluke remained alive after four hours. AT 10 µg, reduced activity was noted at 1, 3 and 4 hours and all were moribund or dead by 7 hours. Reduced activity in some individuals was seen by 24 hours in the 5 µg and 3 µg groups with a somewhat slower onset at 3 µg; all were dead in the 3 and 5 µg treatment wells by 50 hours except one sluggish fluke in each group. Some slowing of activity was noted in the 1 µg group at 42–74 hours and only 3 active and one moribund fluke remained alive at 91 hours; at 115 hours only one sluggish fluke remained in the 1/g group. Mortality in the control with RBC group was observed at 66 hours (one fluke), 91 hours (one fluke) and 115 hours (four flukes). In the Control without RBC group, all were alive at hour 91 and one was dead at hour 115.

Experiment 2: For NTZ, somewhat greater activity was noted by earlier effects on motility score and mortality in the 8 replicates as compared to results for D-NTZ. In the 100, 50 and 25 µg groups all flukes were dead or moribund except one fluke at 1 hour in the 25 µg group it was dead at 3 hour. Dose-related reduction in motility was seen in each of the other medicated groups beginning at hour 1. At 10 µg, only one fluke survived to 16 hours. In the 5 µg group, only 3 flukes were active at hour 6 and none were active at 16 hours. By 23 hours, only 2 sluggish flukes in the 3 µg group remained alive; these ere dead by hour 41. For the 1 µg group, one fluke died by hour 16, three by hour 41 an d vie by hour 74; 3 flukes remained active at hour 91 and one fluke had activity at hour 115. In the Control with RBC group, 7 of 8 flukes were alive at hour 74, 3 were alive at hour 91 and 2 survived at hour 115. In the Control without RBC group, 6 of 8 flukes had activity at hour 74, 4 were active at hour 91 and two remained active at hour 115.

Fluke death in the high dose groups (25, 50, 100 µg) was rapid and associated with contraction and ventral 'curling'. At lower medication levels, most flukes slowed for a period and were more relaxed and 'flattened' when moribund or dead.

Contamination became limiting on experimental results in some replicates beginning at hour 91. For the D-NTZ experiment, major bacterial or fungal overgrowth and associated mortality in two replicate plates occurred by hour 115. For the NTZ experiment, overgrowth and fluke mortality in entire replicate plates occurred by hour 91 (two replicates), and hour 115 (5 replicates). Hour 139 observations were not considered valid because of general contamination of most plates.

Conclusions:

Strong flukecidal efficacy by nitazoxanide is suggested by experiments with both drugs tested. Somewhat greater flukecidal activity against *F. hepatica* was observed for nitaxoxanide than for desacetyl-nitazoxanide, the main metabolite, which is thought to be active at the hepatic level.

Rapid fluke death occurs within 1 hour at in vitro D-NTZ medication rates of >50 µg, within 4 hours at 25 µg and by 6–7 hours at 10 µg. Ten µg, may be an appropriate single treatment target drug delivery rate if pharmacokinetic data indicate tissue levels are maintained for >6–8 hours after a single treatment.

Strong flukecidal activity by 74 hours (three days) was observed for both compounds at the 3 and 5 µg dose rates. Prolonged survival approaching, but not equal to unmedicated control flukes was observed at the 1 µg dose level; delivery of this level of drug to flukes in hepatic tissues for 3 to 4 days may therefore have inadequate therapeutic effect on parasites.

EXAMPLE II

Nitazoxanide was tested against immature and mature *Fasciola gigantica* in experimentally infected rabbits.

*Fasciola gigantica* encysted metacercariae (EMC) were collected on cellophane sheet after 28–35 days from infection of *L. calludi* snails by *Fasciola gigantica* miracidium using the technique described by Abdel-Ghany where snails were exposed daily to artificial light, for 30 minutes, in clean dechlorinated tap water. The resulting encysted metacercaraie (EMC) were preserved at 4° C. in a refrigerator for 5 to 8 days under the surface of water until they were used to infect experimental animals.

Forty (40) Boscat rabbits, weighting 1.5 to 2 kg each, were included in the study and allocated to two treatment groups of 20 animals.

Animals from Group 1 were orally infected with 35–40 encysted metacercarae wrapped in a leaf of lettuce and pushed on the root of the tongue of the animals. The mouths of the animals were held closed by hand until the encysted metacercariae were swallowed. These Group 1 animals were used to test the efficacy of nitazoxanide against immature stages (4–5 weeks old) of *Fasciola gagantica*.

Animals from Group 2 were orally infected as indicated above with 10–15 encysted metacercariae and were used to test the efficacy of nitazoxanide against the early mature flukes (>10 weeks old).

Ten animals from Group 1 received 35 mg of nitazoxanide, morning and evening, for 7 consecutive days 4 weeks after their infection at the immature stage of the parasite cycle. The ten remaining animals in Group 1 were kept as untreated controls.

Ten animals from Group 2 received 35 mg of nitazoxanide, morning and evening, for 7 consecutive days 10 weeks after their infection at the mature stage of the parasite. The 10 remaining animals in Group 2 were kept as untreated controls.

All animals were fed with dry ration until the end of the experiment.

Seven days after administration of the last dose of nitazoxanide, all rabbits from each group were sacrificed. The surface of the liver was examined for the presence of necrotic migrating furrows especially at the immature stage of the parasite cycle. These necrotic areas were examined using two surgical needles in order to extract the juvenile migrating flukes according to the technique described by El-Bahy. The livers were sliced in small pieces especially around the migrating furrows and macerated under a microscope in order to extract the existing flukes. The abdominal cavity and the visceral surfaces were washed with warm water. The water was then collected, sieved and examined for identification of juvenile flukes. All the collected parasites as well as parts of them were counted in both treated and untreated animal in both Groups 1 and 2. Living flukes appeared pin in color, translucid showing intact teguments, easily extractable from the tissue of the livers using warm water, while dead flukes were grayish in color loose and showed a broken necrotic surface. The efficacy of nitazoxanide was calculated by using the formula indicated below:

$$\% \text{ efficacy} \frac{a-b}{a} \times 100$$

Where:
a=the number of flukes recovered from feces in the control animals
b=the number of flukes recovered from feces in the treated animals.

Results

The results of the study as indicated in Table 1 show a marked decrease in the number of immature flukes recovered from the liver of rabbits in the treated group when compared in the control group. The means percentage of reduction was calculated as 46.77% (range: 40–60%).

TABLE (1)

Efficacy of nitazoxanide against immature (4-week/old) F. gigantica in experimentally infected rabbits

| | No. of flukes extracted from liver of | | |
|---|---|---|---|
| Rabbit No. | Untreated Control | Treated rabbits | Efficacy % |
| 1 | 7 | 4 | 42% |
| 2 | 7 | 4 | 42% |
| 3 | 6 | 3 | 50% |
| 4 | 8 | 4 | 50% |
| 5 | 5 | 3 | 40% |
| 6 | 5 | 2 | 60% |
| 7 | 5 | 3 | 40% |
| 8 | 6 | 3 | 50% |
| 9 | 8 | 4 | 50% |
| 10 | 5 | 3 | 40% |
| Mean | 6.2 | 3.3 | 46.77% |

At the early mature stage of their infection, nitazoxanide showed a complete effect (100% reduction) and no worms could be seen after examination of the liver of the treated rabbits in comparison with the untreated control animals as shown in Table 2.

TABLE (2)

Efficacy of nitazoxanide against early mature (10-week/old) F. gigantica in experimentally infected rabbits

| | No. of flukes extracted from liver of | | |
|---|---|---|---|
| Rabbit No. | Untreated Control | Treated rabbits | Efficacy % |
| 1 | 4 | 0.0 | 100% |
| 2 | 4 | 0.0 | 100% |
| 3 | 3 | 0.0 | 100% |
| 4 | 3 | 0.0 | 100% |
| 5 | 2 | 0.0 | 100% |
| 6 | 2 | 0.0 | 100% |

TABLE (2)-continued

Efficacy of nitazoxanide against early mature (10-week/old) F. gigantica in experimentally infected rabbits

| | No. of flukes extracted from liver of | | |
|---|---|---|---|
| Rabbit No. | Untreated Control | Treated rabbits | Efficacy % |
| 7 | 2 | 0.0 | 100% |
| 8 | 3 | 0.0 | 100% |
| 9 | 3 | 0.0 | 100% |
| 10 | 3 | 0.0 | 100% |
| Mean | 2.9 | 0.0 | 100% |

Nitazoxanide administered as a 70 mg/day dose for 7 consecutive days is moderately effective against immature stage of *Fasciola gigantica* and completely effective against the early mature stage of the parasite.

EXAMPLE IV

Nitazoxanide was tested against *Schistosoma mansoni* and *Schistosoma hematobium* in experimentally infected mice.

Forty (40) white mice, weighing 30 to 50 grams were allocated to two treatment groups of 20 animal per group. The first group was infected with 300–500 *Schistosoma mansoni* free active cercariae suspended in 0.25 ml of distilled water and administered to each mouse by intraperitoneal injection. The second group was infected in the same manner but with *Schistosoma hemotobium* cercariae. These two groups were then kept for a total of 70 days in the laboratory.

Seventy days after infection of the animals, ten mice from each group were treated with nitazoxanide as a 1.3 mg oral dose administered, morning and evening, for 7 consecutive days. Seven days after the end of treatment tall mice were sacrificed and the worms were extracted from the liver of each animal by perfusion using tepid water (37° C.). The extracted schistosomes were counted for all treatment and control animals. The efficacy of nitazoxanide was calculated busing the formula indicated below:

$$\% \text{ efficacy} \frac{a-b}{a} \times 100$$

Where:
a=the number of schistosomes recovered from feces in the control animals
b=the number of schistosomes recovered from feces in the treated animals Results The results shown in Tables 3 and 4 clearly indicate that nitazoxanide administered at a daily dose of 2.6 mg/day for 7 consecutive days was more effective against *Schistosoma hematobium* where a worm reduction of 82.85% was observed when compared to the control animals while against *Schistosoma mansoni*, the worm reduction only achieved 59.91% 6 versus the control mice. These results are consistent with those report by Abaza et al. in patients where nitazoxanide was not effective against *S. mansoni* as shown by nitazoxanide post-treatment positive egg-counts.

TABLE (3)

Efficacy of nitazoxanide against mature (13-week/old) *Schistosoma mansoni* in mice

| Mice No. | No. of flukes removed from liver of | |
|---|---|---|
| | Untreated Control | Treated mice |
| 1 | 21 | 10 |
| 2 | 29 | 9 |
| 3 | 32 | 10 |
| 4 | 26 | 11 |
| 5 | 24 | 13 |
| 6 | 19 | 10 |
| 7 | 20 | 9 |
| 8 | 24 | 12 |
| 9 | 22 | 8 |
| 10 | 30 | 7 |
| Total | 247 | 99 |
| Mean/mouse | 24.7 | 9.9 |
| Efficacy | | 59.91 |

TABLE (4)

Efficacy of nitazoxanide against mature (13-week/old) *Schistosoma hematobium* in mice

| Mice No. | No. of flukes removed from liver of | |
|---|---|---|
| | Untreated Control | Treated mice |
| 1 | 18 | 3 |
| 2 | 16 | 3 |
| 3 | 14 | 2 |
| 4 | 19 | 2 |
| 5 | 12 | 4 |
| 6 | 10 | 4 |
| 7 | 13 | 2 |
| 8 | 12 | 2 |
| 9 | 17 | 0.0 |
| 10 | 9 | 2 |
| Total | 140 | 24 |
| Mean/mouse | 14 | 2.4 |
| Efficacy | | 82.85 |

With respect to the above description then, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. A method for treating a parasitic infection of a trematode selected from the group consisting of Schistosoma Fasciola, Fasciolopsis, Dicrocoelium, Heterophyes, and Metagonimus, the method comprising administration of a pharmaceutical composition containing as active agent at least one compound selected the group consisting of a compound of formula I:

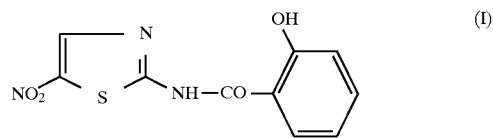

and a compound of formula II:

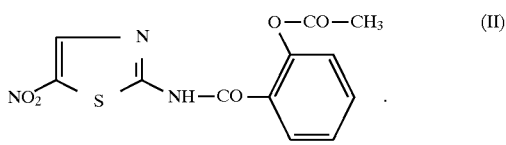

2. A method for treating a parasitic infection of a trematode selected from the group consisting of *Schistosoma mansoni, Schistosoma haematobium, Schistosoma mekongi, Schistosoma japonicum, Schistosoma intercalatum, Fasciola hepatica, Fasciola gigantica, Fasciolopsis biski, Dicrocoelium dendriticum, Heterophyes heterophyes*, and *Metagonimus yokogawa*, the method comprising administration of a pharmaceutical composition containing as active agent at least one compound selected the group consisting of a compound of formula I:

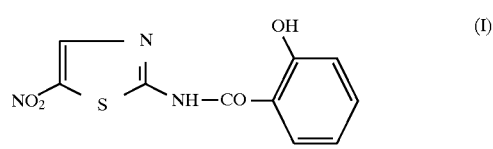

and a compound of formula II:

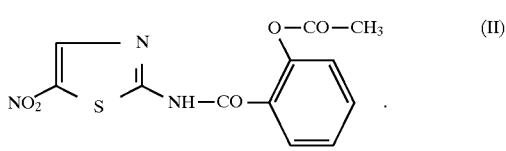

3. A method as in claim 2, wherein said active agent is in the form of particles with a mean particle size of between 10 and 200 $\mu$m.

4. A method as in claim 3, wherein said active agent is in the form of particles with a mean particle size of between 20 and 50 $\mu$m.

5. A method as in claim 3, wherein less than 10% of the said solid particles have a particle size larger than 100 $\mu$m.

6. A method as in claim 2, wherein said pharmaceutical composition contains at least one pharmaceutically acceptable acid.

7. A method as in claim 6, wherein said pharmaceutically acceptable acid is selected from the group consisting of citric acid, glutamic acid, succinic acid, ethanesulfonic acid, acetic acid, tartric acid, ascorbic acid, methanesulfonic acid, fumaric acid, adipic acid, malic acid and mixtures thereof.

8. A method as in claim 6, wherein the ratio of the weight of pharmaceutically acceptable acid/the weight of said active solid particles is between 0.01 and 0.5.

9. A method as in claim 2, which contains as active agent a mixture of solid particles of compounds of formula I and of formula II, the weight content of compound of formula II with respect to the weight of compounds of formula I and of formula II of said mixture is between 0.5 and 20%.

10. A method as in claim 2, wherein said particles of active agent include a granulating agent selected from the group consisting of polyvinylpyrrolidone, water, alcohol, sucrose hydroxyl cellulose and mixture thereof.

11. A method as in claim 2, wherein said trematode is *Schistosoma mansoni*.

12. A method as in claim 2, wherein said trematode is *Schistosoma haematobium*.

13. A method as in claim 2, wherein said trematode is *Fasciola hepatica*.

14. A method as in claim 2, wherein said trematode is *Schistosma mekongi*.

15. A method as in claim 2, wherein said trematode is *Schistosoma japonicum*.

16. A method as in claim 2, wherein said trematode is *Schistosoma intercalatum*.

17. A method as in claim 2, wherein said trematode is *Fasciola gigantica*.

18. A method as in claim 2, wherein said trematode is *Fasciolopsis buski*.

19. A method as in claim 2, wherein said trematode is *Dicrocoelium dendriticum*.

20. A method as in claim 2, wherein said trematode is *Heterophyes heterophyes*.

21. A method as in claim 2, wherein said trematode is *Metagonimus yokogawa*.

22. A method as in claim 2, wherein said active agent is a compound of formula I.

23. A method as in claim 2, wherein said active agent is a compound of formula II.

24. A method as in claim 2, wherein said mammal is human and wherein said active agent is administered in an amount of from 500–2000 mg daily.

25. A method as in claim 24, wherein said active agent is administered in an amount of from 1000–1500 mg daily.

* * * * *